United States Patent
Senko et al.

(10) Patent No.: US 11,764,043 B2
(45) Date of Patent: Sep. 19, 2023

(54) METHODS OF MASS SPECTROMETRY QUANTITATION USING CLEAVABLE ISOBARIC TAGS AND NEUTRAL LOSS FRAGMENTATION

(71) Applicant: Thermo Finnigan LLC, San Jose, CA (US)

(72) Inventors: Michael W. Senko, Sunnyvale, CA (US); Graeme McAlister, San Jose, CA (US); Christopher L. Etienne, Oregon, WI (US)

(73) Assignee: Thermo Finnigan LLC

( * ) Notice: Subject to any disclaimer, the term of this patent is extended or adjusted under 35 U.S.C. 154(b) by 911 days.

(21) Appl. No.: 16/028,932

(22) Filed: Jul. 6, 2018

(65) Prior Publication Data

US 2019/0013188 A1  Jan. 10, 2019

Related U.S. Application Data

(60) Provisional application No. 62/529,382, filed on Jul. 6, 2017.

(51) Int. Cl.
*H01J 49/00* (2006.01)
*G01N 33/68* (2006.01)

(52) U.S. Cl.
CPC ...... *H01J 49/0031* (2013.01); *G01N 33/6848* (2013.01); *G01N 2458/15* (2013.01)

(58) Field of Classification Search
CPC .......... G01N 33/6848; G01N 2458/15; G01N 33/6648; G01N 2468/15; H01J 49/0031

(Continued)

(56) References Cited

U.S. PATENT DOCUMENTS

| | | | |
|---|---|---|---|
| 2004/0157344 A1* | 8/2004 | Wang ................. | G01N 33/6848 556/415 |
| 2008/0014603 A1* | 1/2008 | Fischer .............. | G01N 33/6851 435/23 |

(Continued)

FOREIGN PATENT DOCUMENTS

| | | |
|---|---|---|
| EP | 1918714 A1 | 5/2008 |
| WO | 2006/084130 A2 | 8/2006 |

(Continued)

OTHER PUBLICATIONS

Erickson et al., "Evaluating Multiplexed Quantitative Phosphopeptide Analysis on a Hybrid Quadrupole Mass Filter/Linear Ion Trap/Orbitrap Mass Spectrometer", Analytical Chemistry 87(2), 2015 pp. 1241-1249.

(Continued)

*Primary Examiner* — David E Smith
(74) *Attorney, Agent, or Firm* — Klarquist Sparkman, LLP

(57) ABSTRACT

Isobaric mass spectrometry tags (e.g., TMT) are susceptible to ratio compression, which arises from the co-isolation and co-fragmentation of interfering species that also contribute to the final reporter ion ratios. Additional stages of ion activation/transformation (e.g., MSn and PTR) have been shown to decrease ratio compression. Embodiments of the present invention include a mass spectrometry cleavable moiety on the isobaric mass tags. The cleavable moiety allows for a predictable mass loss, and results in an improved tag reporter ion purity.

20 Claims, 7 Drawing Sheets

(58) Field of Classification Search
USPC ..................................................... 506/9–26
See application file for complete search history.

(56) References Cited

U.S. PATENT DOCUMENTS

| | | | | |
|---|---|---|---|---|
| 2010/0311175 | A1* | 12/2010 | Yan ..................... | C07D 239/54 436/71 |
| 2011/0143951 | A1* | 6/2011 | Thompson ......... | G01N 33/6848 506/7 |
| 2011/0183420 | A1* | 7/2011 | Dey ..................... | G01N 33/743 436/127 |
| 2011/0266426 | A1* | 11/2011 | Schwartz ............ | H01J 49/0045 250/252.1 |
| 2016/0139140 | A1 | 5/2016 | Thompson et al. | |

FOREIGN PATENT DOCUMENTS

| | | |
|---|---|---|
| WO | 2009153577 A1 | 12/2009 |
| WO | 2011091338 A1 | 7/2011 |
| WO | 2013102786 A1 | 7/2013 |
| WO | 2013/112677 A2 | 8/2013 |
| WO | 2015091876 A2 | 6/2015 |
| WO | 2017098029 A1 | 6/2017 |
| WO | 2018141821 A1 | 8/2018 |

OTHER PUBLICATIONS

Karp et al., "Addressing Accuracy and Precission Issues in iTRAQ Quantitation", Molecular & Cellular Proteomics 9.9, 2010, pp. 1885-1897.

Savitski et al., "Delayed Fragmentation and Optimized Isolation Width Settings for Improvement of Protein Identification and Accuracy of Isobaric Mass Tag Quantification on Orbitrap-Type Mass Spectrometers", Analytical Chemistry, 83 (23), 2011, pp. 8959-8967.

Sturm et al., "Improved isobaric tandem mass tag quantification by ion mobility mass spectrometry", Rapid Comm in Mass Spectrometry 28(9), 2014, pp. 1051-1060.

Ting et al., "MS3 eliminates ratio distortion in isobaric multiplexed quantitative proteomics," Nature Methods, vol. 8, No. 11 (20 11), pp. 937-942.

Wenger et al., "Gas-phase purification enables accurate, multiplexed proteome quantification with isobaric tagging", Nature Methods, 8(11), 2011, pp. 933-935.

Extended European Search Report for Application No. 18182241.2, dated Nov. 19, 2018, 11 pages.

Ting L., et al., "MS3 eliminates ratio distortion in isobaric multiplexed quantitative proteomics (Supplementary Information)", Nature Methods, vol. 8, No. 11, Oct. 2, 2011 (Oct. 2, 2011), pp. 937-940, XP055076879, ISSN: 1548-7091, DOI: 10.1038/nmeth.1714.

Rauniyar et al., "Isobaric Labeling-Based Relative Quantification in Shotgun Proteomics," J. Proteome Res. 2014 (13), 5293-5309.

Han et al., "Electron Transfer Dissociation of iTRAQ Labeled Peptide Ions", Journal of Proteome Research (2008), 7, pp. 3643-3648.

Lu et al., "Sulfonium Ion Derivatization, Isobaric StableIsotope Labeling and Data Dependent CID- and ETD-MS/MS for Enhanced Phosphopeptide Quantitation, Identification and Phosphorylation Site Characterization", J. Am. Soc. Mass Spectrom. (2012) 23, pp. 577-593.

Nie et al., "Characterization and multiplexed quantification of derivatized aminophospholipids", International Journal of Mass Spectrometry 391 (2015), pp. 71-81.

Schreiber, "Improving Quantitative Accuracy and Precision of Isobaric Labeling Strategies for Quantitative Proteomics Using Multistage (MS3) Mass Spectrometry", American Laboratory, 2013, vol. 45 (1), pp. 10-13.

Wuehr et al., "Accurate Multiplexed Proteomics at the MS2 Level Using the Complement Reporter Ion Cluster", Anal. Chem. 2012, 84, pp. 9214-9221.

ROCHE Opposition against EP 3 425 405 B1 filed on Dec. 10, 2021.

* cited by examiner

----- = Fragmentation sites

25

27

24

26

----- = Fragmentation sites

----- = Fragmentation sites

------ = Fragmentation sites

METHODS OF MASS SPECTROMETRY QUANTITATION USING CLEAVABLE ISOBARIC TAGS AND NEUTRAL LOSS FRAGMENTATION

FIELD OF THE INVENTION

The present invention relates generally to methods of mass spectrometry (MS) quantitation and more particularly, to methods of producing fragment ions that undergo a neutral loss in at least one of the fragmentation steps.

BACKGROUND OF THE INVENTION

Isobaric mass spectrometry tags are designed to enable identification and quantitation of, for example, proteins in different samples using tandem mass spectrometry. Mass spectrometry Tandem Mass Tags (TMT, Thermo Fisher Scientific, Waltham, Mass.) or iTRAQ tags (AB Sciex LP, Ontario, Canada) are commonly used isobaric chemical labels with different numbers and combinations of heavy isotopic atoms that may include, $^2H$, $^{13}C$, $^{15}N$, and $^{18}O$ heavy isotopes in the mass reporter.

In MS data, peak heights/peak areas or peak ion counts are directly proportional to relative abundance or intensities of the peaks. Areas under two different spectrally pure peaks in the same spectrum may provide an accurate representation of two different ions measured in the spectrum (a quantitative measurement). Quantitation based on TMT is performed by covalently attaching a tag molecule to one or more analyte peptides, usually by reacting a N-hydroxysuccinimide (NHS) ester functional group in a tag with a free primary amino group in the peptide (e.g., a peptide N-terminus or a lysine side chain primary amino group).

Trypsin and Lys-C are two common proteolytic enzymes, which are used in "bottom-up" protein digestion. Trypsin cuts at C-termini of Lysine (Lys) or Arginine (Arg) amino acid residues and Lys-C cuts only at C-termini of Lys residues. As such, each tryptic peptide may be labeled once (cut after an Arg) or twice (cut after a Lys) with isobaric MS tags, assuming that every resulting peptide primary amine is labeled, that only Lys side chains and N-termini are tag labeled, and that there are no missed enzyme cleavages. Irrespective of the enzyme used, there will always be a free amino group on the N-terminus of digested peptides. The situation may be complicated a little further due to missed enzyme cleavages or cuts, which may result in one or more internal Lys residues.

In MS/MS (MS2), or MSn mass spectra, a "reporter ion" may be cleaved from an isobaric tagged peptide by various fragmentation methods, the reporter ion may be detected, and the reporter ion m/z value and peak intensity/height/counts may be measured. The area under a reporter ion mass spectral peak (or the height of the peak) may afford a quantitative measurement of a tagged peptide as the peak area or intensity of the reporter ion peak may be proportional to its relative abundance.

To perform peptide quantitation in a multiplexing manner, a series of isobaric tag molecules may be chemically synthesized that contain various combinations of heavy isotopic atoms (for example, $^2H$, $^{13}C$, $^{15}N$, and $^{18}O$). The "base" tag may contain no heavy isotopic atoms and would not be useful as an isobaric tag. To compile a set of multiplexed isobaric tags from a base tag chemical structure, heavier isotopic atoms may be differentially substituted for their respective naturally occurring most abundant isotopic atoms ($^1H$, $^{12}C$, $^{14}N$, and $^{16}O$) in a balanced way between tag reporter moieties and mass balance regions of the tags. Heavier isotopic atoms are distributed to different parts of the same molecule such that each different tag reagent has the same nominal mass. When a tag reporter ion fragment is produced by MS/MS fragmentation, each tag reporter ion in the series should have a different m/z value. Tag reporter ions may either have differing nominal masses, as in the case for the TMT 6-plex, or they may have a mixture of differing nominal masses and differing fractional masses (due to a mass defect effect), as in the case for some of the TMT 10-plex. A series of samples (e.g., peptide mixtures) may be labelled with unique TMT tags using a series of multiplexed isobaric labels, and then the samples may be pooled and quantitatively analyzed concurrently.

An example of a "base" TMT tag is shown in Scheme 1.

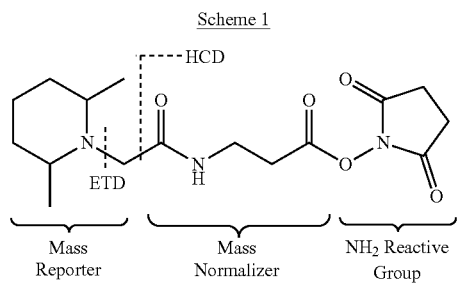

Scheme 1

Different MS fragmentation methods may yield different types of reporter tag fragments from the same TMT tag. For example, in Scheme 1, fragmentation by collision induced dissociation (CID) or by higher collision induced dissociation (HCD) may produce different tag reporter ions than the reporter ions produced by electron transfer dissociation (ETD).

A two-plex isobaric MS tag kit sold by Thermo Fisher Scientific (Waltham, Mass.) contains the two isobaric MS tags shown in Scheme 2.

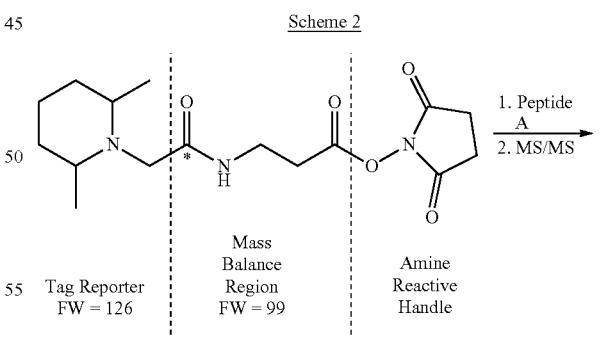

Scheme 2

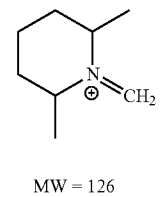

MW = 126

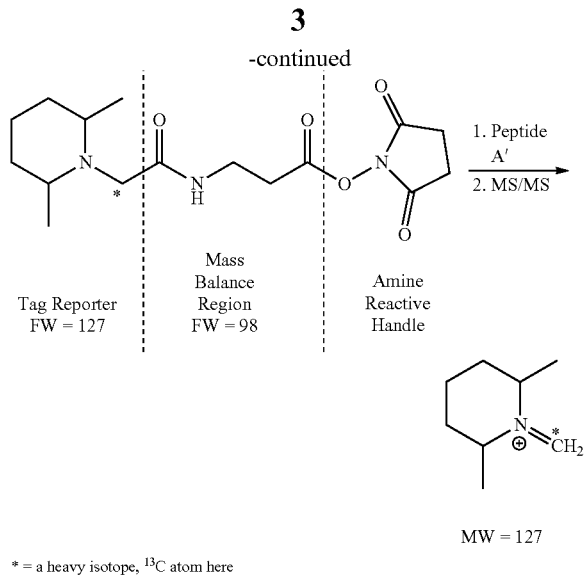

* = a heavy isotope, $^{13}$C atom here

The molecular weights of both whole tags in the two-plex kit are the same (isobaric), but upon MS/MS fragmentation, Peptide A would yield a tag reporter fragment with a nominal m/z of 126 Da and Peptide A' would yield a tag reporter fragment with a nominal m/z of 127 Da. These m/z values are about one whole dalton apart, and are therefore easily baseline resolvable in any commercial tandem mass spectrometer.

In Scheme 2, Peptides A and A' represent peptides with the same primary structure, but come from two different sources. For example, in some bioassays, Peptide A may be from a selected tryptic peptide derived from a specific cellular protein from a normal cell. Peptide A' having exactly the same atomic chemical structure as Peptide A, comes from the same cellular protein but may be derived from a diseased cell. The diseased cell may contain higher or lower levels of the specific protein (for example due to genetic upregulation or down-regulation, respectively), in which case the specific protein (or the selected tryptic peptide from that protein) may be used as a biomarker for the disease in question.

Two clinical LC-MS/MS samples may be prepared as follows: a specific protein from a normal cell may be extracted from a particular type of cell, digested with an enzyme such as trypsin or Lys-C, and the resulting digested peptides may be labeled with one or more MS isobaric tags, for example, the TMT tag that generates a 126 Da reporter ion. The same procedure may be used for the same cell type from a patient carrying a particular disease. The resulting digested peptides in this case may be labeled with an MS isobaric tag that generates a 127 Da reporter ion. At this point, the two samples may be combined and subjected to LC-MS/MS quantitative analyses. The selected labeled peptide from each sample should elute from a reversed phase LC separation with substantially the same retention time, even though the two labeled peptides have different isotopically-labeled MS isobaric tags. Digested and tagged peptides from different samples with identical peptide sequences will produce indistinguishable intact (MS1) m/z values. As such, these tagged reporter ions may then be isolated together for MS/MS quantitative analysis. Subsequently, unique tag reporter ions may be generated in the MS/MS spectrum (126 and 127 in this case), and the proteins from the different cell sources may be quantified by comparing the relative intensities, areas, or heights of the unique tag reporter ions.

Reporter ions for a TMT 6-plex commercial kit have tag reporter ion fragments at m/z ratios of 126, 127, 128, 129, 130, and 131. Each of the different TMT reagents has the same intact nominal mass and the same basic chemical molecular structure. They are comprised of three main components: a cleavable tag reporter moiety that may contain different levels of stable isotope enrichment at various atoms; a mass balance region that may contain different levels of stable isotope enrichment at various atoms for the sake of "balancing" the enrichment in the cleavable tag; and a chemically reactive handle that facilitates covalent peptide tagging. Stable isotopes in each of the individual isobaric tags are distributed across the MS2 labile bond, such that the heavy isotopes in the tag reporter moiety are balanced by the heavy isotopes in the mass balance region. For example, for a TMT 6-plex, reporter ions that break off during a MS2 fragmentation step yield quantitative tag reporter ions that have unique nominal masses for each of the six TMT reagents (m/z=126-131).

Quantitative analysis between different reporter ion intensities are susceptible to errors termed "ratio compression" that are also known as "ratio distortion". A major cause to ratio distortion has been identified as the co-isolation and co-fragmentation of interfering or extraneous ions during the isolation and fragmentation steps of analytes of interest. The bulk of these background ions will produce tag reporter ion intensity ratios with a 1:1 "normal" value. With respect to the earlier example, if the measured ratio is 1:1, then that indicates that the amount of selected biomarker peptide in the normal (control) cell is the same as the amount from a patient's cell, and therefore the patient may not have the disease in question. The most likely ratio of any experiment over the whole comparative range of analyzed cellular proteins is a 1:1. The ratios seen in actual experiments are typically compressed towards 1:1 (Karp, Natasha A., et al., Molecular & Cellular Proteomics 9(9), 2010, pp. 1885-1897) resulting in a more than desirable false negative result rate. Several methods have been proposed to minimize this ratio compression, including proton transfer reactions (Wenger, Craig D., et al., Nature methods, 8(11), 2011, pp. 933-935); MS3 (Ting, Lily, et al., Nature methods 8(11), 2011, pp. 937-940); ion mobility separation (Sturm, Robert M., Christopher B. Lietz, and Lingjun Li., Rapid Communications in Mass Spectrometry 28(9), 2014, pp. 1051-1060); and triggering delays (Savitsk, Mikhail M., et. al., *Analytical chemistry*, 83 (23), 2011, pp. 8959-8967). All of these methods do reduce the observed ratio distortion; however, they also require other sacrifices either by requiring complex scan sequences that reduce the breadth of coverage, complex ion manipulation steps that reduce the sensitivity of the method, or a limited overall improvement in the measured ratio compression. Therefore there is a need to address the problem of ratio distortion in isobaric tag quantitation in a more efficient manner.

A recent publication on the use of TMT for the quantitative analysis of phosphopeptides reported that limiting a MS3 precursor population to just a phosphate neutral loss was sufficient to provide significantly more accurate ratio measurements (Erickson. Brian K., et al. *Analytical chemistry* 87(2), 2015 pp. 1241-1249). Against the above background, there is a need for the development of tandem mass tags that circumvent or significantly reduce ratio distortion in quantitative isobaric tag analyses.

SUMMARY OF THE INVENTION

In embodiments of the present invention, a mass spectrometry analyte (for example, a peptide, protein, small molecule, glycan or nucleic acid) is labeled with a MS isobaric tag to form a tagged analyte which contains a tag reporter, a mass balance region, and a neutral loss group. The labeling process may typically involve chemically reacting a MS tag NHS ester with any free primary amines present in peptide analytes, for example, there may be free primary amino groups at the N-terminus or at any lysine amino acid side-chains present in a peptide. The tagged analyte may then be ionized in an ion source of a mass spectrometer to form a first precursor ion. Common types of ion sources that may be used include electrospray ionization (ESI), atmospheric chemical ionization (APCI), atmospheric pressure photoionization (APPI), and matrix-assisted laser desorption ionization (MALDI). The precursor ion may be selected for fragmentation. Selection of a precursor ion(s) can include isolation of a specific precursor ion or precursor ions in a three dimensional (3D) ion trap, a two dimensional (2D) ion trap, a dual pressure two dimensional linear ion trap, or may involve mass filtering of a specific precursor ion or ions by a quadrupole mass filter. Following isolation, a precursor ion may undergo a first fragmentation. A first fragmentation step of a precursor ion or ions may be achieved by a variety of fragmentation methods including, ultraviolet photodissociation (UVPD), collision induced dissociation (CID), higher energy collisional dissociation (HCD), infrared multiphoton dissociation (IRMPD), electron capture dissociation (ECD), electron transfer dissociation (ETD), negative ion electron transfer dissociation (NETD), pulsed Q dissociation (PQD), or some combination of the above techniques (for example IRMPD concurrent with ETD, AI-ETD).

Fragmentation may produce at least one neutral loss fragment (wherein the neutral loss fragment is large comprised of the neutral loss moiety) together with at least one first generation fragment (or product) ion. Precursor ions containing only one isobaric MS tag may only lose one neutral fragment and form only one main product ion. Precursor ions containing two isobaric MS tags may lose one or two neutral loss fragments, and therefore may produce one or two main product ions, and so on. In this case, sequential activation may be used, for example, sequential CID activation, to remove more than one neutral fragment at a time. As an additional example, prolonged energetic activation may be used to remove more than one neutral fragment (e.g., by using prolonged UVPD irradiation times).

Alternatively, a method of product ion parking may be used which may involve the application of a resonance excitation voltage tuned to inhibit further fragmentation of one or more specific product ions. For example, UVPD activation may be used together with resonance excitation to remove a product ion(s) over a specific m/z range(s) from further dissociation by essentially manipulating trap ion containment voltages to enable product ion(s) to reside out of the path of the laser beam that produces UVPD fragmentation. At least one of the first generation of the neutral loss product ions containing a tag reporter moiety may then be fragmented to afford a second generation of product ions, wherein a tag reporter moiety is cleaved to form a tag reporter fragment ion. The tag reporter ion may then be quantitatively mass analyzed, and from this information the amount of an enzymatically digested peptide analyte may be deduced that should coincide with the amount the peptide's parent protein.

Some examples of isobaric tags that may be used in this method include:

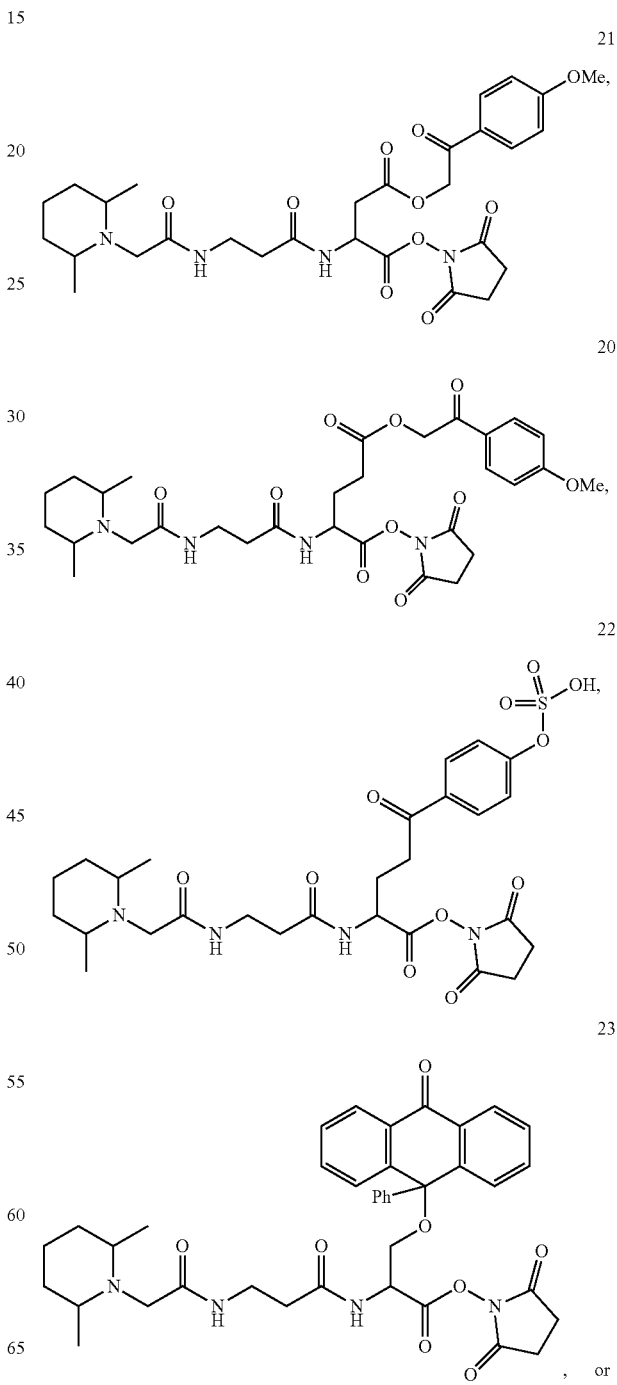

33

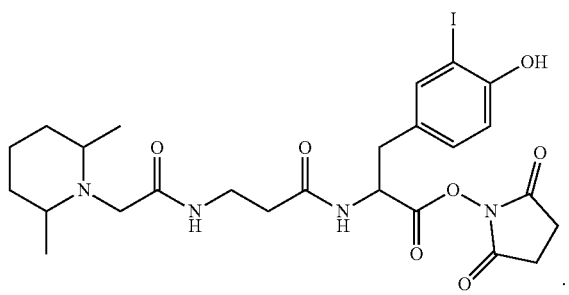

BRIEF DESCRIPTIONS OF THE DRAWINGS

DETAILED DESCRIPTION

Figure 1:
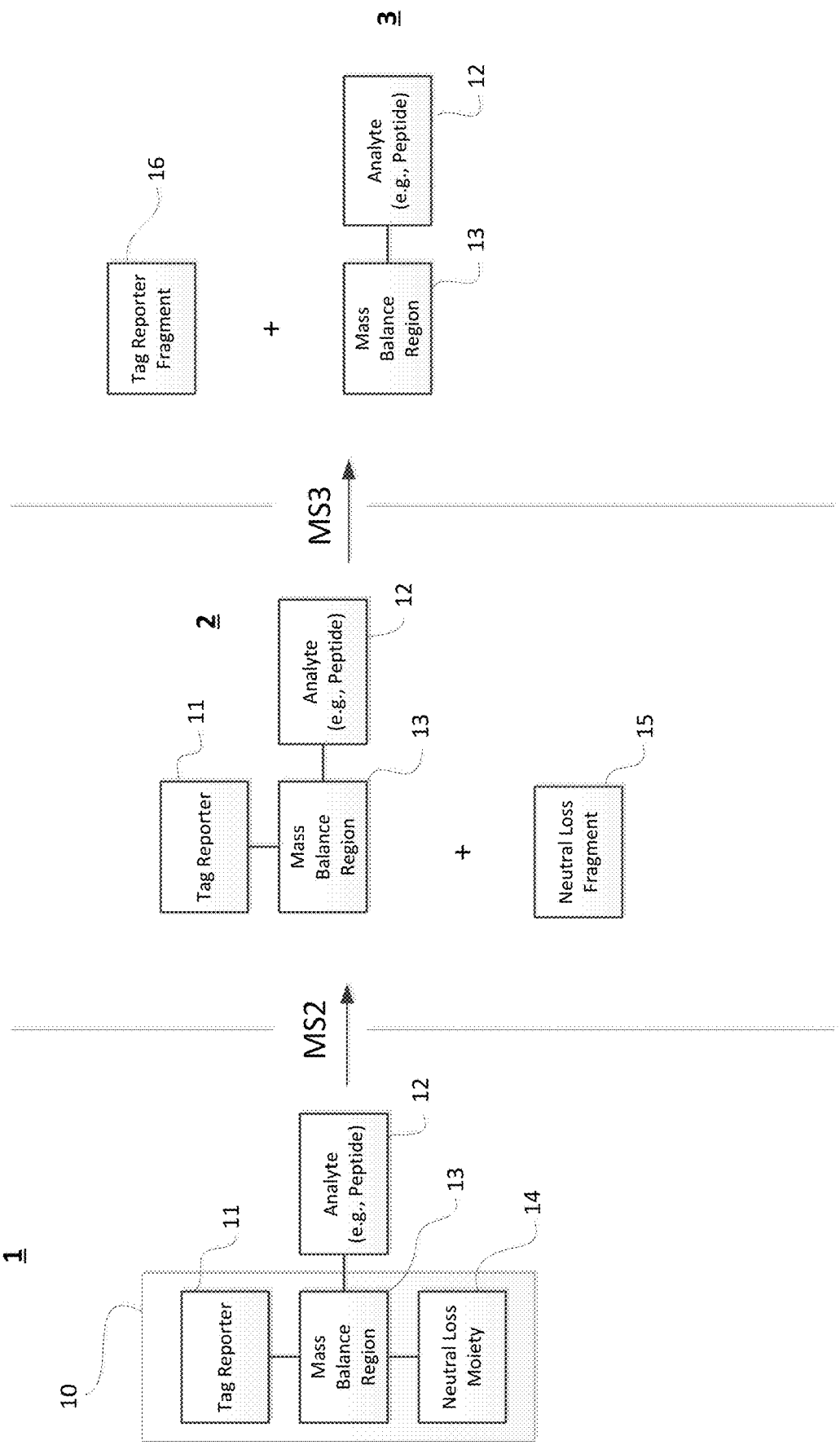
FIG. 1 shows a flow chart of two MS/MS steps on an analyte labeled with one TMT tag.

The terms "tag", "MS tag", "TMT", "TMT tag", "isobaric tag" or "isobaric MS tag" as used herein refer generally to a molecular entity comprising a molecular tag reporter moiety, where heavy stable atomic isotopes are substituted at one or more atomic positions in the molecule. They include a tag reporter moiety, a mass balance region, a chemically reactive handle, and, optionally, a neutral loss moiety. Isobaric tags may be further defined as being a chemical label, for example, a tandem mass tag (TMT). TMT tags are well-known isobaric mass spectrometry stable isotope labels that are commonly used in multiplexed mass spectrometry assays, for example, to quantitate a selected set of peptides from one source with a selected set of peptides from one or more different sources. The term "analyte" as used herein means a molecule that will be analyzed in a mass spectrometer. An analyte peptide may be underivatized (label-free) or it may be chemically derivatized with a TMT label. A molecule may be derivatized with a TMT label that facilitates LC-MSn quantitation. The term "conjugate" as used herein means a chemically derivatized analyte (e.g., a labeled peptide or protein). A peptide with a primary amine at its N-terminus may react with an isobaric MS tag containing a N-hydroxysuccinimide ester (a NHS ester) functional group to produce a "peptide-MS tag" molecule.

The term "peptide" as used herein means an amino acid based polymer usually composed of some combination of the twenty common naturally-occurring amino acids, but may also contain or be completely composed of unnatural amino-acid monomer residues. It may indicate a linear amino acid polymer configuration, or may include a cyclic peptide, or a branched one, or any combination of all three configurations. A peptide may also have any combination of naturally occurring modifications (e.g., phosphorylation or glycosylation) or unnaturally occurring modifications (e.g., carbamidomethylation). The term protein as used herein means a relatively large amino acid polymer based biomolecule which comprises one or more peptide chains, and may contain metal ions or other adjunct atomic or molecular entities, for example, as enzyme co-factors.

The term "isobaric" means having the same nominal molecular weight or formula weight. The term, "multi-notch" is used to describe a well-known process for simultaneously isolating two or more ions in an ion trap. The term "base" isobaric tag or "base" MS tag means a tag that has not been enriched with any stable heavy isotopic atoms. Enrichment with alternatively balanced stable heavy isotopic atoms may make an isobaric tag series suitable for use in multiplexing assays. The term "cleavable bond" or "cleavable linker" means a covalent chemical bond that may be broken in an activation/fragmentation process in a mass spectrometer. The term, "trypsin peptide" or "tryptic peptide" is used herein to describe any analyte peptide produced in a bottom-up mass spectrometry protein analysis. This may be a peptide derived from digesting a protein with trypsin or with Lys-C or with any other proteolytic enzyme. The term, "stable isotope" or "stable isotope label" or "stable heavy isotope" means a compound that has one or more heavy isotopic atoms (for example, $^2$H, $^{13}$C, $^{15}$N, and $^{18}$O) in place of their respective (normally) highest abundant naturally occurring elemental isotope ($^1$H, $^{12}$C, $^{14}$N, and $^{16}$O). This allows for tight control of atomic isotopes at various positions in the molecule.

Ratio distortion is a well-known problem that occurs frequently when using isobaric tags in mass spectrometry analysis. The problem arises when targeted precursor analyte ions are co-isolated and co-fragmented with interfering ions that are also conjugated to isobaric tags. Both co-fragmented target and interfering ions produce the same reporter ions. As such, the "true" reporter ion ratios of targeted precursors can be obfuscated by the contribution of reporter ions derived from interfering ions. Depending upon sample complexity, and experimental conditions, ratio distortion problems can be quite severe. For example, in bottom-up proteomic analysis, a plurality of (cell) proteins may be trypsin (or otherwise) digested into hundreds or thousands of analyte tryptic peptides, many of which have near identical m/z ratios. They may be poorly resolved by both liquid chromatography and MS1 m/z analysis, and may contain interfering ions. During analysis of a typical experimental sample, the median reporter ratio will likely most often be 1:1 or "un-changed" (for example, when comparing tryptic peptide ratios for proteins from a "normal" cell to those of a diseased cell). This type of ratio distortion caused by interfering ions causes "ratio compression", which in-turn leads to an underestimation of statistically significant reporter ratios. Including an additional round of MS selectivity (e.g., MS3 analysis), may obviate the signal contribution from interfering ions. In other cases the interfering ions may distort the ratios away from 1:1, in which case the observed data would falsely indicate that the protein abundances are different between the samples when in-fact the abundances are the same. In other cases the interfering ion signals are by-products of the ionization and ion-injection process, and are not simply co-eluting tryptic peptides.

Provided herein are MS processes that significantly reduce the contribution of interfering ions to the final reporter ion population. Novel isobaric mass tags for use in the described methods are also included. In particular, MS methods are described that involve the formation of a loss of a neutral fragment and a first product ion in a first fragmentation step. This is followed by a second fragmentation step that generates tag reporter ions. The use of neutral loss fragments, in combination with MS methods that involve multiple fragmentation steps, provides a distinct advantage over existing MS methods using only one round of fragmentation (e.g., MS2). By increasing the MS selectively (for example, by generating a neutral loss fragment during primary fragmentation and then selecting the resulting product ion for secondary fragmentation) the methods disclosed herein can yield MS spectra of tag reporter ions that are more accurate as compared to existing techniques.

In some embodiments herein, an analyte (for example, a peptide) is labeled with an isobaric tag containing a tag reporter moiety, a neutral loss moiety, and a mass balance region to form a tagged analyte. The tagged analyte may then be ionized in an ion source of a mass spectrometer to form a tagged analyte precursor ion. An analyte-MS tag conjugate precursor ion (tagged analyte or tagged analyte precursor) may be fragmented at least twice in a mass spectrometer. In a first fragmentation process, a charged product ion is produced together with at least one neutral loss fragment. A neutral loss fragment cannot be further confined or analyzed by a mass spectrometer's ion optical system as it would not be containable by the instrument's electric fields. Subsequently, the charged product ion (fragment ion) from the first fragmentation process may undergo a second fragmentation process that releases a charged tag reporter ion that may be used for analyte quantification.

A two fragmentation process as described above may involve the same type of fragmentation process, for example, both may involve higher energy collision dissociation (HCD), or they may involve different types of fragmentation processes (for example, UVPD followed by CID or vice versa). Embodiments of the present invention may involve a neutral loss moiety that is linked to the mass balance region of an isobaric tag. In other embodiments, a neutral loss moiety may be appended, for example, as a chemical substituent group, directly to a tag reporter moiety. In this case, the neutral loss moiety would necessarily have to be removed during a first fragmentation step before a second fragmentation step produced the quantitative tag reporter ion.

A basic MS scan sequence is shown in FIG. 1. An analyte mixture (for example, a mixture of peptides) 12 may be labeled with an isobaric mass spectrometry tag 10 to form an analyte-MS tag conjugate 1 containing the analyte 12, a tag reporter 11, a mass balance region 13, and a neutral loss moiety 14. Conjugate 1 may be ionized in a mass spectrometer ion source, and may undergo a first round of precursor ion isolation and activation, for example, activation using HCD, CID, ETD or UVPD for a first neutral loss fragmentation step. After a first activation and fragmentation process, a first product ion 2 (tag reporter 11, mass balance region 13 and analyte 12) may be isolated minus its neutral loss fragment 15. In other embodiments, the isolation step may be skipped in-favor of fragmenting the first product ion 2 while all the other product ions possibly formed in the first fragmentation step are retained in the trap.

In a second round of fragmentation, the first product ion 2 may be fragmented, for example, by HCD, to give a tag reporter fragment ion 16, and an analyte 12 that may be still be conjugated to the mass balance region 13 of the MS tag (connected together as 3 shown in FIG. 1). The tag reporter fragment ion 16 may be used to quantify the analyte 12, while the analyte-mass balance region conjugate 3 may be further fragmented to provide sequence informative fragment ions for the analyte peptide. These subsequent analyte fragment ions may be used, for example, to confirm a target analyte peptide sequence. In some embodiments, the sequence informative fragment ions and the tag reporter fragment ions are generated during the same fragmentation step. In this later embodiment, some of the sequence informative fragment ions may still be conjugated to both the mass balance region and the tag reporter moiety.

Figure 2:
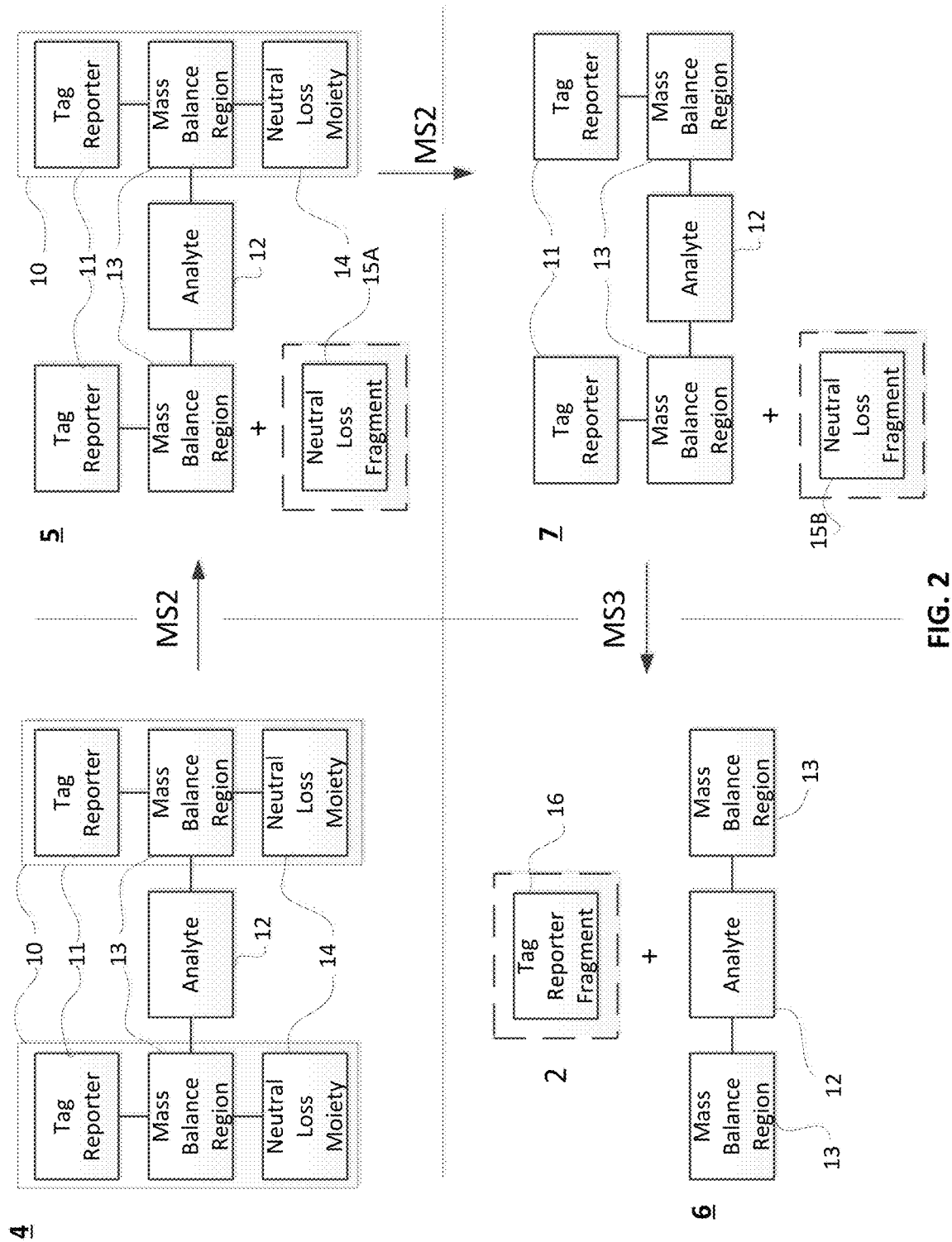
FIG. 2 shows a flow chart of a MS2 step followed by a MS3 step followed by a MS4 step on an analyte labeled with two TMT tags.

FIG. 2 shows a similar process whereby an analyte 12 is labeled with two isobaric mass spectrometry tags 10 to afford an analyte-tag conjugate 4. In this case an analyte is doubly labeled and contains two neutral loss moieties 14. At least a portion of 4 may only lose one of the neutral loss moieties depending upon fragmentation conditions used during the first fragmentation process (for example, limited exposure time and/or energy imposed on the ion during the first fragmentation step). As shown in the top right hand quadrant of FIG. 2, the analyte-MS tag conjugate only loses a single neutral loss moiety 14 after a first fragmentation process. A first round of fragmentation may afford a neutral loss fragment 15A together with a product ion 5. Additional first step fragmentation (pseudo MS3 fragmentation or "multistage activation") may afford product ion 7 together with the loss of a second neutral loss fragment 15B, that is, both neutral loss moieties may be lost from product ion conjugate 4. A second round of fragmentation may be performed to give product ion 6. This may occur with a loss of one or both tag reporters 11. As shown in FIG. 2, both tag reporters 16 are lost during the second fragmentation step. As above, 6 may be further fragmented to provide sequence informative fragment ions that can be used to confirm or identify a peptide analyte. As above, isolation step proceeding the second round of fragmentation may be skipped in favor of fragmenting 7 in the presence of other fragment ions generated during the first round of fragmentation. As above, the sequence informative ions and tag reporter fragments may be generated concurrently as a result of the second round of fragmentation.

Figure 3:
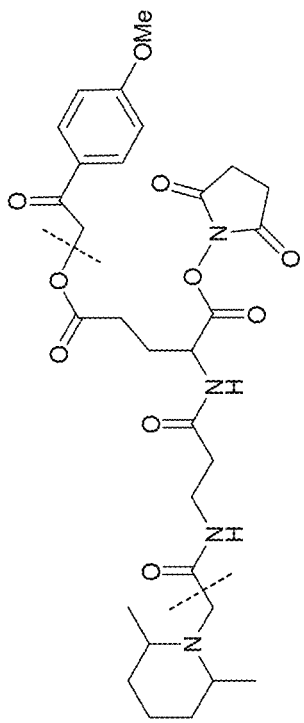
FIG. 3 shows four compounds that may lose a neutral loss moiety during UVPD fragmentation (UVPD cleavage sites shown on the right hand side of each structure).
Figure 3:
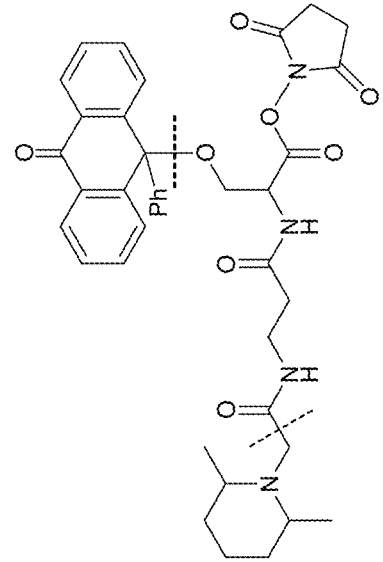
Figure 3:
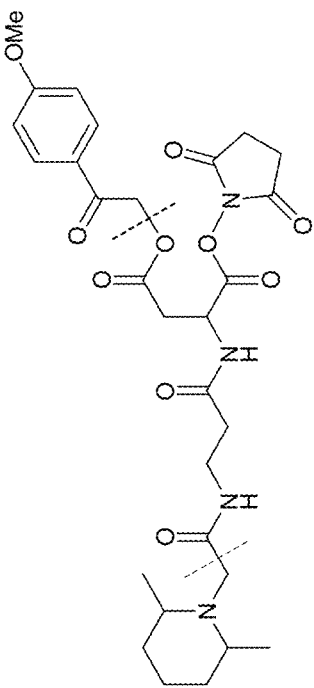
Figure 3:
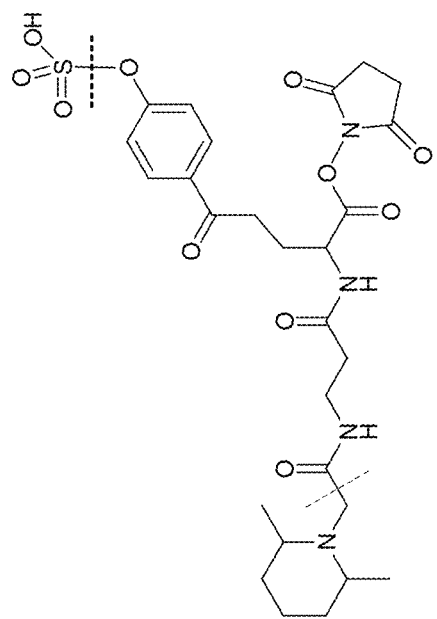

FIG. 3 shows four exemplary MS tag NHS esters, 20, 21, 22 and 23. These compounds may be "base" tags (not labeled with any heavy stable isotopic atoms). Each base tag shown may be a foundational base compound from which a series of heavier isobaric MS tags may be prepared. This would entail varying the amounts of heavy isotopic atoms, for example, $^{13}C$ or $^{15}N$ throughout the structural series of isobaric tags. Each isobaric tag would have the same molecular weight and the same molecular structure as the base tag, but all isobaric tags would have the same nominal molecular weight difference when measured against the base tag.

Referring to Scheme 3, isobaric tag NHS ester 20 may react with a peptide analyte that has an arginine amino acid residue at its C-terminus (for example, from a trypsin digest).

Scheme 3

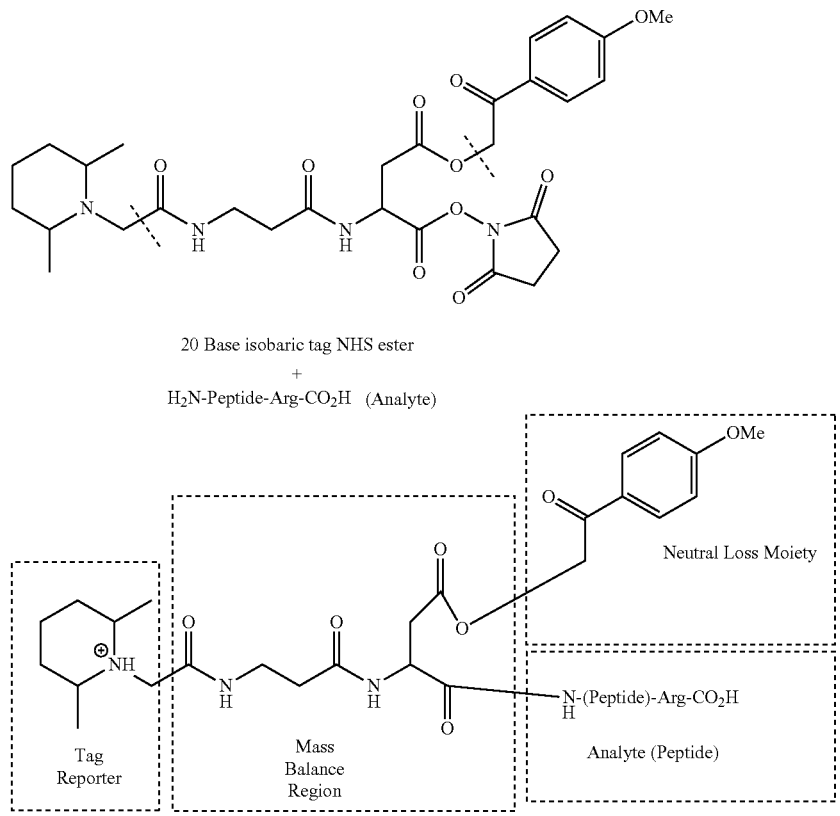

In this exemplary case the peptide analyte has only one free amino group at its N-terminus.

Each tag-analyte conjugate has many potential fragmentation sites depending upon the length of the peptide and on the chemical structure of the MS tag. As shown by the small dashed lines on the base isobaric tag 20 in Scheme 3, these particular isobaric tags have two preferred conventional (CID or HCD) fragmentation sites.

Scheme 4

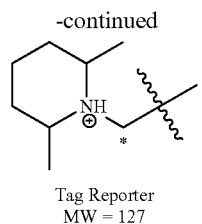

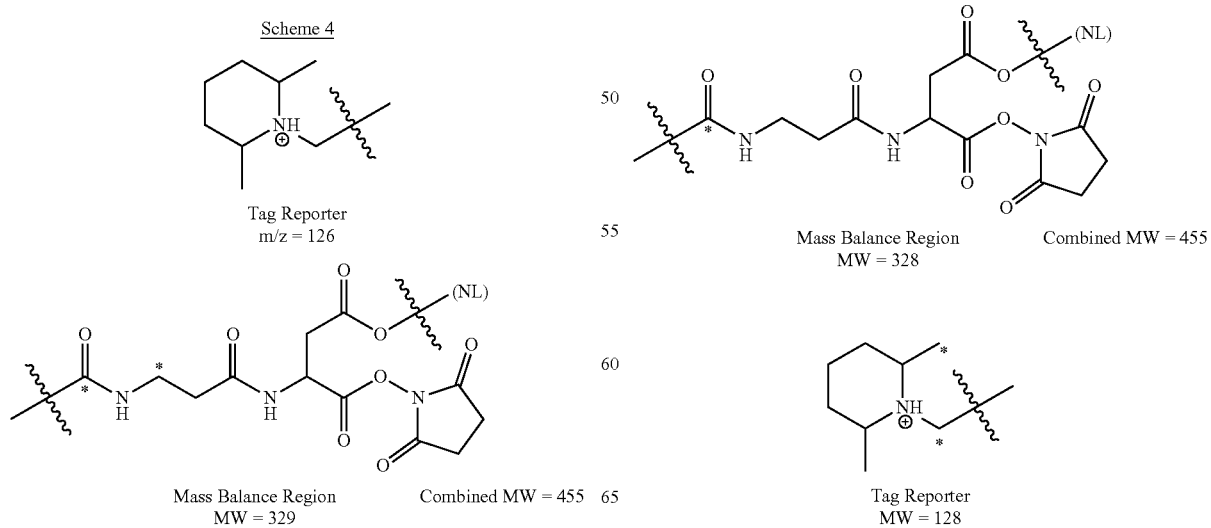

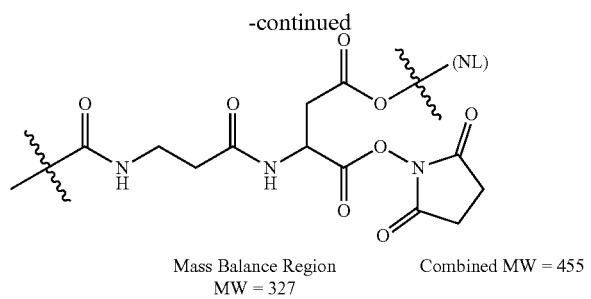

Mass Balance Region  Combined MW = 455
MW = 327

\* = enriched with a $^{13}$C atom

The fragmentation site on the right hand side is where the neutral loss moiety is cleaved from the tag (or from the tag-peptide conjugate after conjugation of a tag to a peptide). The fragmentation site on the left hand side is where the tag reporter moiety is cleaved from the tag (or from the tag-peptide conjugate) under, for example, CID or HCD fragmentation conditions. Under ETD or ECD fragmentation conditions, the left-hand side fragmentation site may occur one bond to the left of that shown in structure 20 (a C—N bond as opposed to a C—C bond).

Scheme 4 shows an example of components that may be present in a 3-plex multiplexing kit. Tag reporter moieties, mass balance regions, and NHS esters for each label are shown. Neutral loss moieties are labeled "(NL)". All neutral loss moieties are the same here but for simplicity, are not counted in "combined molecular weights" (MW) shown in scheme 4. The molecular weight of each isobaric tag is 455 Da. Their tag reporter moieties are sequentially separated by 1 Dalton, such that from top to bottom in Scheme 4 each tag reporter moiety contains one more enriched $^{13}$C heavy isotopic atom. To keep the tags isobaric, each time a $^{13}$C is substituted for a normal $^{12}$C in a tag reporter moiety, a $^{12}$C is substituted for a $^{13}$C in the corresponding mass balance regions.

In some embodiments herein, six-plex multiplexing kits may be compiled where, for example, the tag reporter and the mass balance region add up to 458. The kits may contain tag reporter moieties that may have between zero, one, two, three, four or five atomic positions that are enriched with one to five $^{13}$C atoms (or $^{15}$N atoms, or $^{2}$H atoms, or a combination of these heavy isotopic atoms), and wherein the molecular weight of the cleaved reporter moieties would range from 126 to 131 Da. To keep the tags isobaric, the mass balance regions need to be enrich with sufficient heavy isotopes to balance the enrichment in the reporter ion. For example, consider the tags shown in Scheme 4, in this case the mass balance region may range from 332 to 327 Da by a similar substitution of heavy isotopic atoms. Table 1 shows a summary of this example. The above examples show how MS isobaric tags described in the present invention may be used in multiplexing kits using nominal masses (approximately 1 Da differences between the tag reporter moieties).

TABLE 1

| Tag Reporter MW (Da) | Mass Balance Region MW (Da) | Sum of Tag Reporter + Mass Balance Region (Da) |
|---|---|---|
| 126 | 332 | 458 |
| 127 | 331 | 458 |
| 128 | 330 | 458 |
| 129 | 329 | 458 |
| 130 | 328 | 458 |
| 131 | 327 | 458 |

A higher degree of multiplexing may be achieved using tags that contain isotope substitutions other than $^{13}$C atoms in place of $^{12}$C atoms. For example, by using a combination of isotopically enriched $^{13}$C and $^{15}$N atoms, and then measuring the m/z of a tag reporter fragment by high resolution accurate mass (HRAM), the number of multiplexing channels may be increased. This HRAM analysis may be achieved by the using a mass spectrometer with an OrbiTrap™ or TOF mass analyzer, or with FT-ICR-based mass spectrometers. For example, due to mass defects, an isobaric tag with a tag reporter ion that contains two $^{13}$C atoms will have slightly different molecular weight than one that contains one $^{13}$C and one $^{15}$N atom. High end HRAM mass spectrometers may be able to resolve peaks for these two different isotopic tag reporter ions that have the same nominal mass.

These examples are in no way meant to limit the scope of the present invention to the number of multiplexing components in the above exemplary MS tag kits, and are purely for illustrative purposes.

As tagged analyte molecules described herein may include more than one tag label (for example, as described above, peptides with a C-terminal Lys may be labeled with two isobaric tags) an initial activation step in an ion trap may be performed in "pseudo-MS3" mode. Also sometimes referred to as "multistage activation". In this case, precursor ion 4 in FIG. 2 may be initially activated to afford a single neutral loss fragment 15A that may get pumped away by the vacuum system, and a product ion 5 (this is 4 minus a neural loss fragment 15A) that remains confined in the ion trap. This product ion 5 may be activated to break the second cleavable bond to release a second neutral loss fragment 15B. Isolation of the resulting product ion 7 may occur after the second neutral loss, but isolation may optionally be performed after the first neutral loss, or, both 5 and 7 may be isolated in a multi-notch isolation mode of operation. Alternatively, no isolation may occur between any of the activation steps in FIG. 2, or only minimal isolation may occur to remove the inadvertent tag reporter ions generated during the first round of fragmentation (but the other fragment ions are retained in the trap).

Other methods of handling tag conjugates with multiple labels may involve using a prolonged activation time (for example, when using UVPD fragmentation), or a prolonged ion reaction time (for example, when using ETD). In either case, the elongated reaction time might be combined with a product ion parking process. Product ion parking involves fragmentation using, for example, UVPD with resonant excitation of the desired fragment ion. This guarantees that all tagged precursors undergo, for example, only a single neutral loss independent of the number of tags conjugated to the precursor ion. This may be achieved, for example, in an ion trap using a laser for UVPD fragmentation, by moving a selected product ion out of the path of the laser immediately after it has undergone a first neutral loss fragmentation. The selected product ion may be moved out of the laser path by resonantly exciting the ion in the trap so that it resides outside of the laser beam's path.

Cleavable bonds that attach neutral loss moieties to an isobaric MS tag need not be restricted to only labile bonds that are broken via collisional activation. In alternative embodiments of the present invention, a neutral loss moiety may be attached to a tag by a bond that is susceptible to photodissociation techniques. A phosphate moiety that may be susceptible to collisional activation may also be susceptible to IRMPD or UVPD. Further embodiments of the present invention involve ETD cleavable bonds, for example, conjugates that contain disulfide linkers such as 35 in FIG. 6.

The use of a photocleavable bond may be favored over a collisionally activated bond as a photocleavable bond may be less likely to prematurely cleave in a mass spectrometer (for example, by in source fragmentation). Attaching a neutral-loss moiety using a CID cleavable bond may be further complicated, as this bond may be more labile than any other bond in the analyte-MS tag conjugate. Such a bond should be sturdy enough so that the labeled conjugate precursor ion does not prematurely fragment during ionization, injection, transport, or ion trapping. Inclusion of a photocleavable bond may obviate these concerns as in many cases, a photo-cleavage process may be orthogonal to a CID mechanism. A tag labeled analyte conjugate precursor ion may be isolated and irradiated with photons of an appropriate wavelength, followed by a second isolation at an m/z value that corresponds to the neutral-loss product ion, followed by collisional activation to generate a tag reporter ion together with sequence informative ions from a peptide analyte that may be used to confirm or identify the analyte. This same workflow may be applied to linkers that are susceptible to electron/ion fragmentation or ion/molecule processes (for example, as in ETD fragmentation processes).

Another embodiment involves a base MS tag compound 20 in FIG. 3. MS tag 20 (as shown in Scheme 3 above) has tag reporter group, a mass balance region, and a methoxyphenacyl neutral loss moiety. The methoxyphenacyl group may be selectively photo-cleaved using UV light of around 190 to 300 nm. Phenacyl groups (PhCOCH$_2$—) are commonly used photo-labile protecting groups in organic synthesis. A tryptic peptide analyte may be labeled with base MS tag 20, or may be labeled with a stable isotope labeled version of 20 (as used for multiplexing kits), to afford a tagged peptide. The tagged peptide may be ionized in an ion source of a mass spectrometer to form a first precursor molecular ion. The precursor ion may then be selected and fragmented, for example, by UVPD fragmentation to generate a neutral phenacyl fragment and a first generation fragment ion containing the peptide analyte. The first generation fragment ion may then be selected and fragmented to lose its tag reporter ion which may be used for quantitative mass analysis of the analyte peptide. Another co-isolated first generation fragment ion may concomitantly fragment to form peptide sequence informative fragment ions (for example, b- or y-ions).

Figure 4:
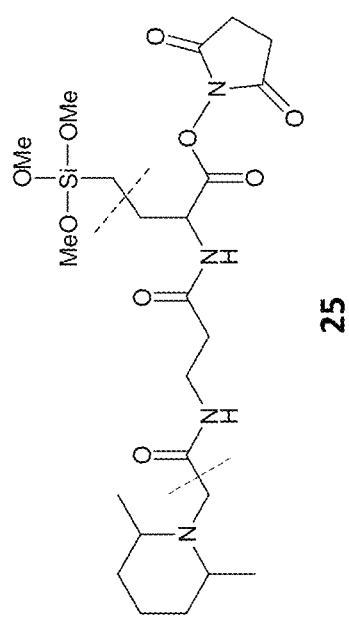
FIG. 4 shows four compounds that may lose a neutral loss moiety during UVPD fragmentation (UVPD cleavage sites shown on the right hand side of each structure).
Figure 4:
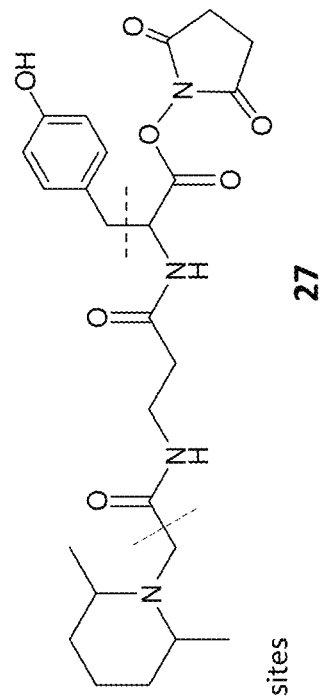
Figure 4:
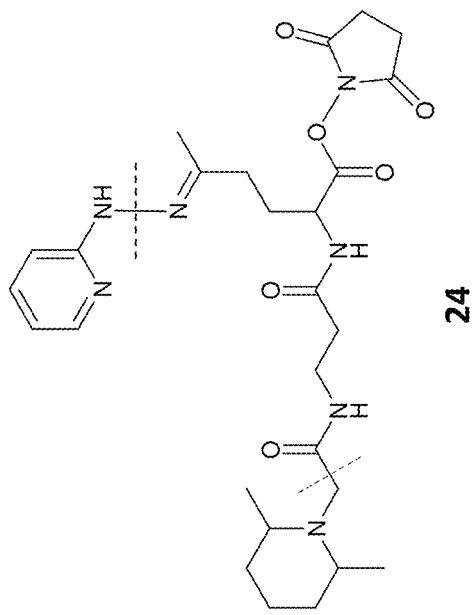
Figure 4:
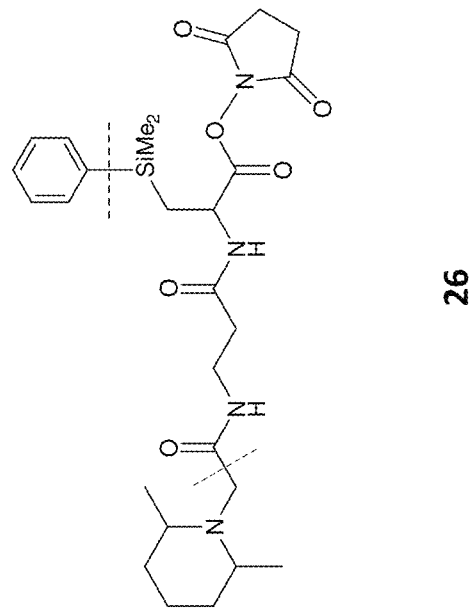
Figure 5:
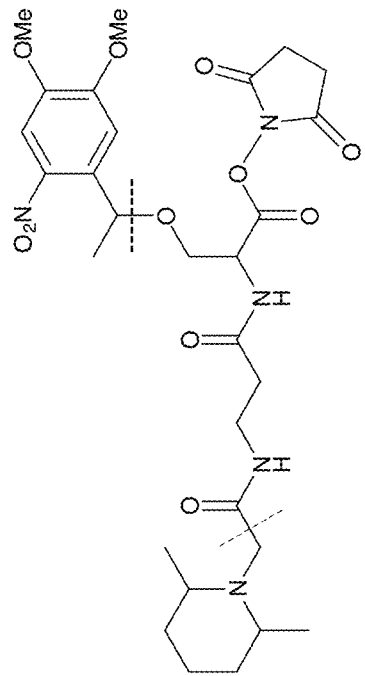
FIG. 5 shows four compounds or types of compound that may lose a neutral loss moiety during UVPD fragmentation (UVPD cleavage sites shown on the right hand side of each structure).
Figure 5:
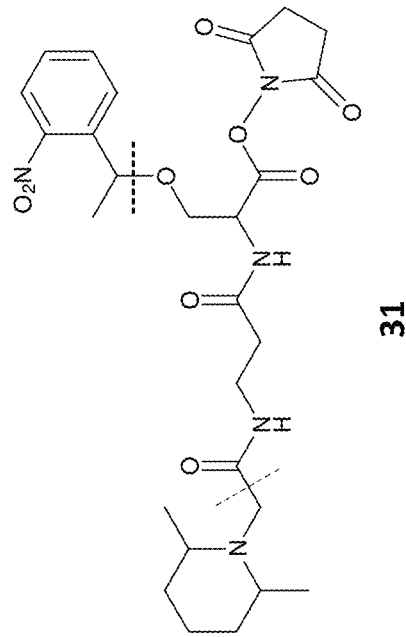
Figure 5:
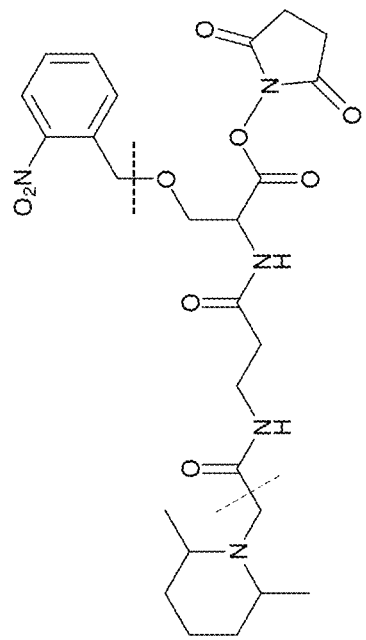
Figure 5:
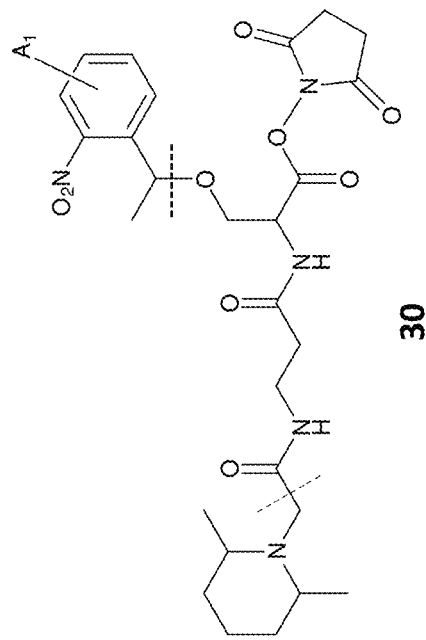
Figure 6:
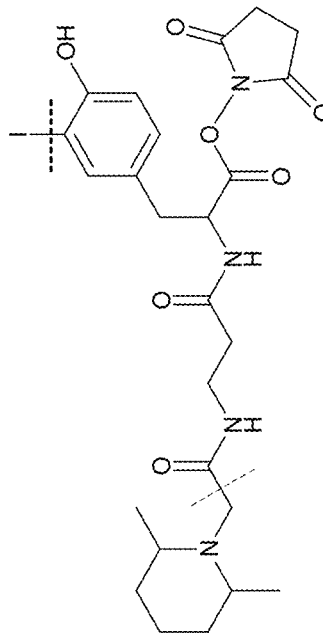
FIG. 6 shows three compounds, 32, 33 and 34 which may lose a neutral loss moiety under collisional induced dissociation (CID or HCD) fragmentation or by UVPD fragmentation, and 35 which may lose a neutral loss moiety under electron transfer dissociation (ETD) fragmentation conditions (disulfide ETD cleavage sites shown on the right hand side of 35).
Figure 6:
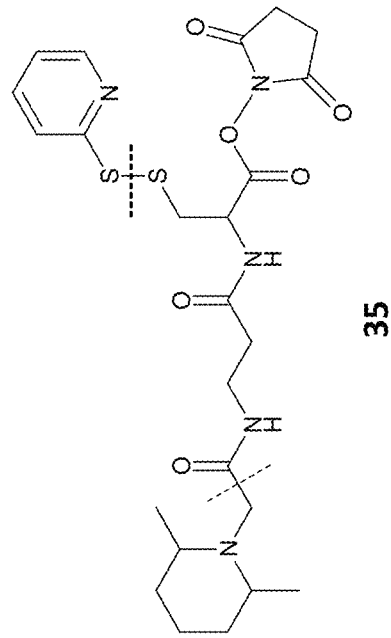
Figure 6:
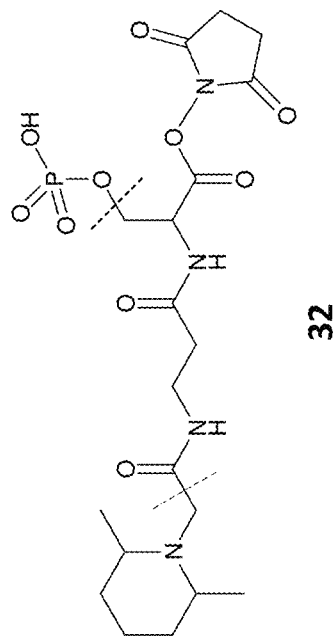
Figure 6:
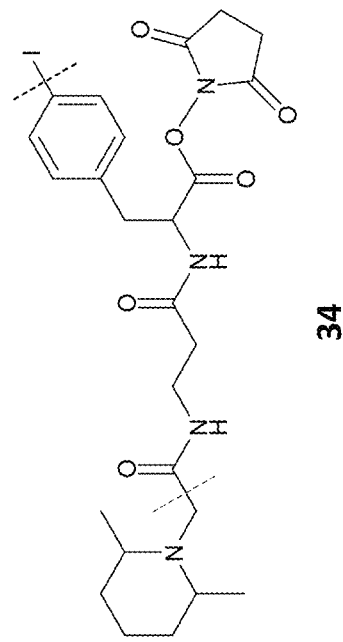

Alternative embodiments suitable for neutral loss UVPD fragmentation include base mass tags 21, 22 and 23 in FIG. 3; also 25, 26 and 27 in FIG. 4; also 28, 29, 30 and 31 in FIG. 5; and, 32, 33 and 34 in FIG. 6. Base mass tags 32, 33 and 34 in FIG. 6 show examples of base isobaric mass tags that may undergo neutral loss more efficiently either under CID fragmentation or under UVPD conditions, depending on the conditions, losing either a phosphate radical or iodine radical (iodine atom).

Alternatively, base mass tags 24 in FIGS. 4 and 33 in FIG. 6 may operate more efficiently under ETD fragmentation conditions.

Figure 7:
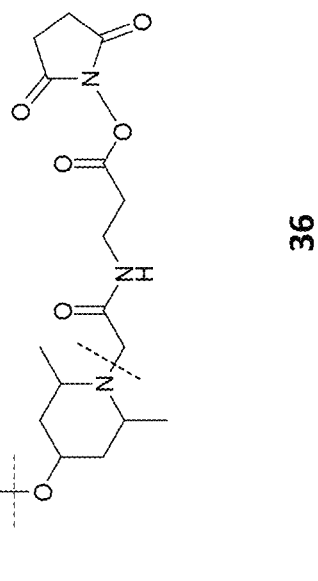
FIG. 7 shows a specific compound 36 and a general schematic block representation 37, both depicting a neutral loss group attached to a tag reporter moiety.
Figure 7:
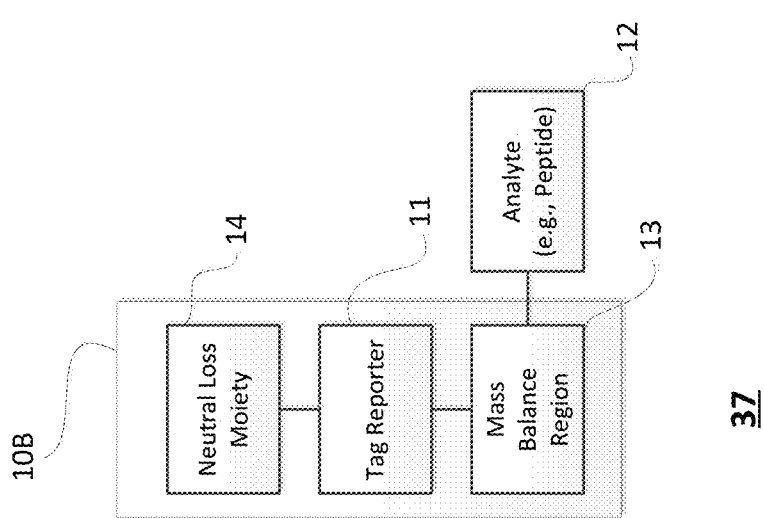

FIGS. 1-6 show neutral loss moieties attached to tag mass balance regions, however, a neutral loss moiety may be attached to a tag reporter moiety as exemplified in structure 36 and shown generically in 37 (FIG. 7).

Analytes other than peptides may be analyzed by this method. For example, alternative analytes may include peptoids, glycans, lipids, fatty acids, small molecules, polymers, polyethylene glycols or nucleic acids. Depending upon the analyte being labeled, alternative reactive functional group may be employed to conjugate the tag to the analyte. For example, a carbonyl containing analyte may be labeled using an amide reactive group (as in the aminoxy TMT tags).

A comparable method may be practiced where a conventional TMT tagged peptide analyte may be appended with a neutral loss moiety, for example, by conjugating a neutral loss moiety containing a primary or secondary amino group to the C-terminus (or to a side chain carboxylate group) of a tagged analyte peptide. This may be achieved by using a variety of amidation methods that one skilled in the art would be familiar with, for example, by using a water soluble carbodiimide coupling reagent, or, by preparing an activated ester at the peptide C-terminus, for example, an NHS ester, and then reacting this with a neutral loss fragment containing a primary or secondary amino group. The effect of this would be to shift the neutral loss moiety location to somewhere on an analyte peptide instead of having it appended to a tag mass balance region or to a tag reporter moiety.

Specific embodiments as described herein incorporate details to facilitate the understanding of the inventive concept, as well as principles of construction and operation of the invention. Such reference herein to specific embodiments and details thereof is not intended to limit the scope of the claims appended hereto. It will be readily apparent to one skilled in the art that various other modifications may be made in the embodiments chosen for illustration without departing from the spirit and scope of the invention as defined by the claims. For example, one skilled in the art would recognize that there are very large number of molecular variants that may be substituted for neutral loss moieties 14, tag reporter moieties 11 and mass balance regions 13 in FIGS. 1, 2 and 7 without departing from the spirit and scope of the invention.

What is claimed is:

1. A method of mass spectrometry, comprising:
   (a) labeling a peptide with an isobaric tag comprising a tag reporter moiety, a neutral loss moiety and a mass balance region to form a tagged peptide;
   (b) ionizing the tagged peptide to form a precursor ion;
   (c) selecting the precursor ion for fragmentation;
   (d) in a first fragmentation, fragmenting the precursor ion to form a first generation of fragment ions and a neutral loss fragment, wherein the neutral loss fragment is, or is at least a part of, the neutral loss moiety, and in a first mass analysis, mass analyzing the first generation of ions and the neutral loss fragment;
   (e) selecting at least one of the first generation of fragment ions for fragmentation; and
   (f) in a second fragmentation, fragmenting the at least one first generation of fragment ions to form a second generation of fragment ions, wherein the second generation of fragment ions includes a tag reporter ion, and in a second mass analysis, mass analyzing the tag reporter ion, wherein the first mass analysis and the second mass analysis are the only mass analyses.

2. The method of claim 1, wherein the peptide is labeled with a plurality of isobaric tags.

3. The method of claim 1, wherein a plurality of peptides are labeled with a series of isobaric tags, wherein the plurality of peptides may be from the same source or from different sources and where the plurality of peptides have the same amino acid sequence.

4. The method of claim 1, wherein ionizing the tagged peptide is performed using ESI, APCI, MALDI or APPI.

5. The method of claim 1, wherein the peptide is sequenced concurrently or after the tag reporters are mass analyzed.

6. The method of claim 1, wherein fragmenting the precursor ion to form a first generation of fragment ions is performed using UVPD.

7. The method of claim 1, wherein fragmenting the precursor ion to form a first generation of fragment ions is performed using HCD, CID, ETD, NETD or ECD.

8. The method of claim 1, wherein fragmenting the precursor ion to form a first generation of fragment ions is performed using IRMPD.

9. The method of claim 1, wherein fragmenting at least one of the first generation of fragment ions to form a second generation of fragment ions is performed using PQD.

10. The method of claim 1, wherein fragmenting the first generation of fragment ions to form a second generation of fragment ions is performed using HCD, IRMPD or CID.

11. The method of claim 1, wherein fragmenting the first generation of fragment ions to form a second generation of fragment ions is performed using ETD, NETD or ECD.

12. The method of claim 1, wherein fragmenting the first generation of fragment ions to form a second generation of fragment ions is performed using HCD or IRMPD.

13. The method of claim 1, wherein the first and/or second generations of fragment ions are mass analyzed in an orbitrap mass analyzer.

14. The method of claim 1, wherein the first and second generations of fragment ions are mass analyzed in a quadrupole, ion trap, FT-ICR or time of flight mass analyzer.

15. The method of claim 1, wherein the neutral loss fragment is attached to a mass balance region of the isobaric tag.

16. The method of claim 1, wherein the neutral loss fragment is attached to the tag reporter moiety of the isobaric tag.

17. The method of claim 2, wherein the peptide labeled with multiple tags is fragmented using UVPD with resonant excitation whereby all precursor ions undergo only a single neutral loss.

18. A method of mass spectrometry, comprising:
(a) labeling a peptide with an isobaric tag comprising a tag reporter moiety, a neutral loss moiety and a mass balance region to form a tagged peptide;
(b) ionizing the tagged peptide to form a precursor ion;
(c) selecting the precursor ion for fragmentation;
(d) fragmenting the precursor ion to form a first generation of fragment ions and a neutral loss fragment, wherein the neutral loss fragment is, or is at least a part of, the neutral loss moiety;
(e) selecting at least one of the first generation of fragment ions for fragmentation;
(f) fragmenting the at least one first generation of fragment ions to form a second generation of fragment ions, wherein the second generation of fragment ions includes a tag reporter ion; and (g) mass analyzing the tag reporter ion, wherein the isobaric tag is,

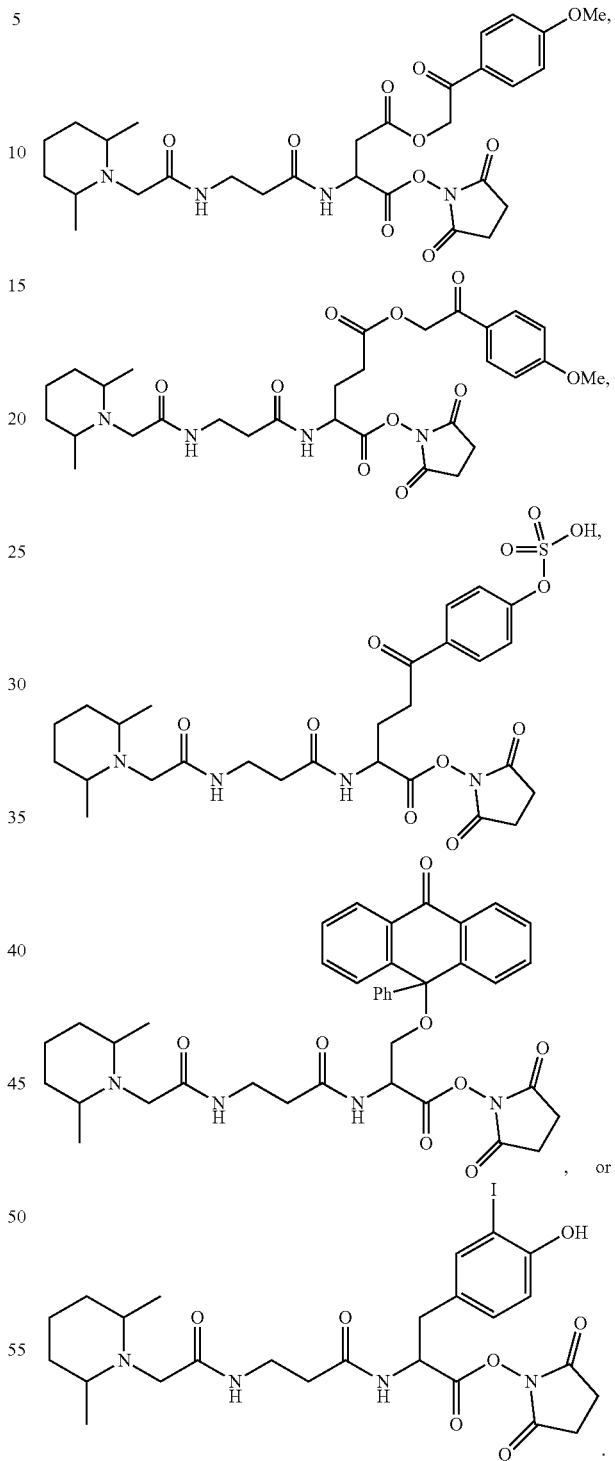

19. A method of mass spectrometry, comprising:
(a) labeling an analyte with an isobaric tag comprising a tag reporter moiety, a neutral loss moiety and a mass balance region to form a tagged analyte;
(b) ionizing the tagged analyte to form a precursor ion;
(c) selecting the precursor ion for fragmentation;

(d) in a first fragmentation, fragmenting the precursor ion to form a first generation of fragment ions and a neutral loss fragment, wherein the neutral loss fragment is or is at least a part of the neutral loss moiety, and in a first mass analysis, mass analyzing the first generation of ions and the neutral loss fragment;

(e) selecting at least one of the first generation of fragment ions for fragmentation; and (f) in a second fragmentation, fragmenting the at least one first generation of fragment ions to form a second generation of fragment ions, wherein the second generation of fragment ions includes a tag reporter ion, and in a second mass analysis, mass analyzing the tag reporter ion, wherein the first mass analysis and the second mass analysis are the only mass analysis.

20. The method of claim 19 wherein the analyte is a protein, peptoid, glycan, lipid, fatty acid, small molecule, polymer or nucleic acid.

\* \* \* \* \*